United States Patent [19]

Maijer et al.

[11] Patent Number: 4,478,576
[45] Date of Patent: Oct. 23, 1984

[54] ORTHODONTIC ATTACHMENT PLACEMENT DEVICE

[75] Inventors: Rolf Maijer, Duncan; James W. Starck, Victoria, both of Canada

[73] Assignee: Romada Holdings Ltd., Duncan, Canada

[21] Appl. No.: 503,623

[22] Filed: Jun. 13, 1983

Related U.S. Application Data

[63] Continuation-in-part of Ser. No. 383,712, Jun. 1, 1982, Pat. No. 4,424,029.

[51] Int. Cl.³ .............................................. A61C 7/00
[52] U.S. Cl. ...................................................... 433/3
[58] Field of Search ............................................ 433/3

[56] References Cited

U.S. PATENT DOCUMENTS

| 3,871,098 | 3/1975 | Dean | 433/3 |
|---|---|---|---|
| 4,035,919 | 7/1977 | Cusato | 433/3 |
| 4,422,849 | 12/1983 | Diamond | 433/3 |

Primary Examiner—Robert Peshock
Attorney, Agent, or Firm—Sim & McBurney

[57] ABSTRACT

Placement devices for positioning orthodontic attachments, such as, brackets, on the lingual and facial side of teeth are described. A tooth engagement plate or other member, which engages the facial side of a tooth for lingual placement or the lingual side for facial placement, is mounted for pivotal movement at least about a horizontal transverse axis. An orthodontic bracket holder is mounted to a handle for both horizontal and vertical movement to permit placement of an orthodontic bracket on the opposite side of a tooth to that engaged by the plate. In operation, for lingual placement, the tooth engagement plate is positioned in engagement with the facial side of the tooth, the bracket is located in its desired position adjacent the lingual side of the tooth by up and down movement of the handle and vertical movement of the bracket holder. The bracket, to which adhesive is applied, is drawn into engagement with the lingual side of the tooth to grip the tooth between the front plate and the bracket until the adhesive has cured sufficiently to adhere the bracket to the tooth. The bracket then is released and the device is removed from the mouth. The same procedure is used for facial placement, except that the plate engages the lingual side and the bracket is drawn into engagement with the facial side.

30 Claims, 9 Drawing Figures

ORTHODONTIC ATTACHMENT PLACEMENT DEVICE

REFERENCE TO RELATED APPLICATION

This application is a continuation-in-part of our application Ser. No. 383,712 filed June 1, 1982 now U.S. Pat. No. 4,424,029 issued Jan. 3, 1984.

FIELD OF INVENTION

The present invention relates to a placement device for the positioning of orthodontic brackets or other orthodontic attachments on the lingual or facial side of teeth.

BACKGROUND TO THE INVENTION

The placement of orthodontic brackets on teeth requires the exercise of considerable skill and accuracy to ensure correct treatment of a patient. A variety of positioning instruments are available to place brackets on the outer or facial surface of teeth but none permits complete accuracy of positioning and maintaining that position while the bonding adhesive sets.

More recently, a new orthodontic technique has been utilized in which orthodontic attachments are made on the tongue or lingual side of the teeth. A transfer tray is currently available to locate one or more brackets on the inside of teeth. The fabrication of transfer trays for single teeth is both time consuming and expensive. Such trays, nevertheless, are utilized in the absence of an adequate alternative.

SUMMARY OF INVENTION

In accordance with the present invention, there is provided an orthodontic attachment placement instrument or device which is able to accurately and positively hold and position orthodontic attachments, including brackets, tubes and auxiliaries, at various vertical heights on both the lingual and facial surfaces of both anterior and posterior teeth.

The instrument of the invention includes a tooth engaging member mounted to a handle of the instrument for engagement with one side of a tooth and an orthodontic attachment holder independently connected to the handle for bringing an orthodontic attachment into engagement with the opposite side of a tooth and for gripping the attachment to the tooth between the holder and the member while bonding adhesive cures.

The orthodontic attachment holder is movable in a horizontal direction towards and away from the tooth engaging member so as to bring an orthodontic attachment into engagement with the opposite side of a tooth when the member is in engagement with the one side of the tooth. The vertical position of the attachment holder with respect to a tooth surface is also movable, so that the orthodontic attachment may be located at a desired vertical location on the opposite side of the tooth.

DESCRIPTION OF PREFERRED EMBODIMENTS

Figures 1, 3, 4:
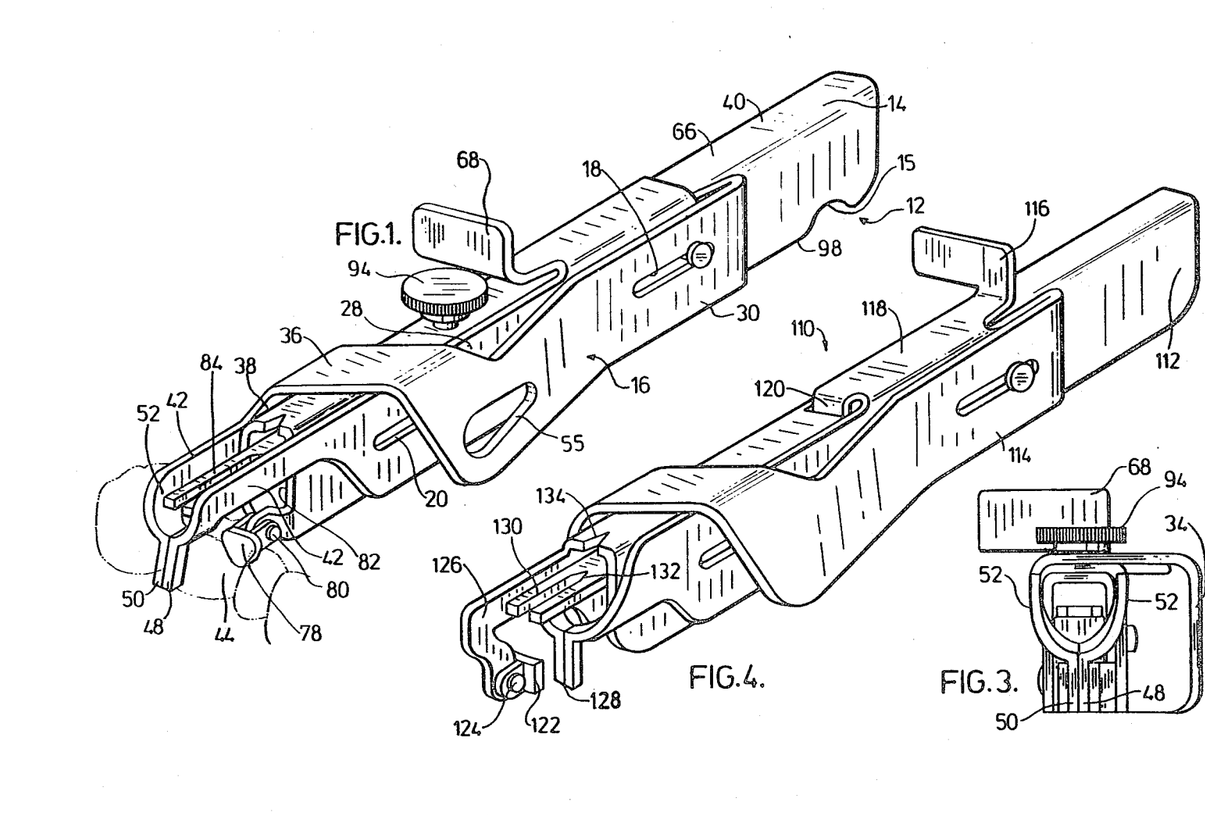
FIG. 1 is a perspective view of an orthodontic bracket placement device for the lingual placement of brackets, constructed in accordance with one embodiment of the invention.
FIG. 3 is a front end view of the device of FIG. 1.
FIG. 4 is a perspective view of an orthodontic placement device for the facial placement of brackets, constructed in accordance with another embodiment of this invention.
Figure 2:
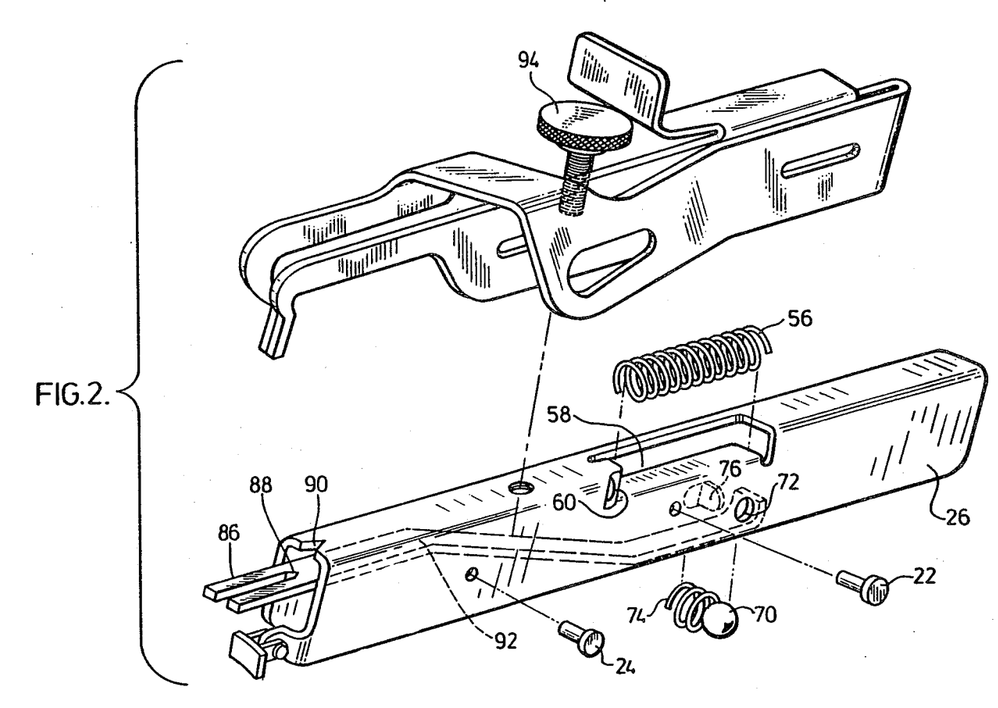
FIG. 2 is an exploded perspective view of the device of FIG. 1.

Referring first to FIGS. 1 to 3, there is illustrated therein a lingual placement device 10 constructed in accordance with a preferred embodiment of the invention. The device 10 includes a handle 12 comprised of two handle members 14 and 16.

The handle member 14 is of elongate hollow structure of substantially inverted U-channel cross section and may have a finger notch 15 formed adjacent the rear end thereof. The handle member 16 is slidably mounted to the handle member 14 by the provision of elongate slots 18 and 20 in the handle member 16 which receive pins 22 and 24 mounted to one side 26 of the handle member 14. The pins 22 and 24 have heads which are larger than the transverse dimension of the slot.

The handle member 16 includes a first elongate plate member 28 which is slidably mounted in face-abutting relationship with the side 26 of the hollow handle member 14 and a second plate member 30. The second plate member has a portion 32 extending in face abutting relationship with the first plate member 28, a portion 34 diverging outwardly away from the first plate member 28, a portion 36 bridging the handle member 14 and a portion 38 extending parallel to the opposite side 40 of the handle member 14.

The handle member 16 includes elongate arms 42 extending one from each member portion 28 and 30 parallel to each other to form a bridge over a tooth 44. Orthodontic attachment holding jaws 46 are provided at the extremities of the arms 40. The jaws 46 comprise a pair of vertically-depending fingers 48 and 50 located generally in alignment with the vertical centre line of the handle member 14, as may be seen in FIG. 3. The jaws 48 and 50 are joined to the arms 42 by members 52 which form a generally U-shape when viewed in elevation (see FIG. 3).

The handle member 16 is constructed of resilient rigid material, such as, spring steel, so that an orthodontic attachment, such as an orthodontic bracket 54, may be gripped between the jaw fingers 48 and 50. The application of pressure, such as, by a thumb, to the divergent portion 34 to cause movement towards the plate member 28 causes the jaw fingers 48 and 50 to open as jaw finger 50 moves away from jaw finger 48, thereby releasing the grip on the orthodontic bracket 54, while release of the pressure permits the divergent portion 34 to be resiliently restored to its rest position and cause the jaws 46 to close. A teardrop shaped opening 55 may be provided in the divergent portion 34 to assist in locating a pressure-applying thumb on the surface thereof.

The handle member 16 normally is biased by a compression spring 56 to a retracted position with respect to the handle member 14. The compression spring 56 is located in an elongate recess 58 in the handle member 14 and engages, at one end, an abutment 60 formed in the handle member 14. A tab 62 depending from the rearward end of an elongate portion 64 of the member 28 slidably engages the upper surface 66 of the handle member 14. An upwardly-extending lever 68 is provided at the forward end of the elongate portion 64 to permit the handle member 16 to be moved forwardly towards an extended position thereof with respect to the handle portion 14, as the spring 56 is compressed.

The face of the plate member 28 abutting side 26 of the handle member 14 is engaged by a ball or roller 70 which extends through a tapered opening 72 in the side 26 of the handle 14 under the influence of a compression spring 74 mounted on a tab 76 extending inwardly of the handle member 14 from the side 40. The ball 70 serves as a stop member to rearward movement of the handle member 16 when in its fully extended forward position of the handle member 16. The ball 70 moves into the tapered opening 72 under the influence of the spring 74 as the rearward end of the handle member 16 passes the opening. The stop may be released by applying rearward pressure to the lever 68.

A tooth engaging plate 78 is pivotally mounted to a horizontal transverse pivot 80 which is provided at the lower end of the open end 82 of the handle member 14. The plate 78 is intended to engage the facial side of the tooth 44 while the orthodontic bracket 54 is drawn into engagement with the lingual side of the tooth 44 under the influence of the compression spring 56. The bracket 54 is then gripped in engagement with the tooth between the jaws 46 and the plate 78.

In a modification of the device of FIGS. 1 to 3, the tooth engaging plate 78 may be constructed of light transmitting material and a light-emitting source, such as a source of visible light or a source of ultraviolet light, may be associated with the plate 78. This construction permits light-curing adhesives to be used to bond the orthodontic attachment, such as bracket 54, to the tooth. While the bracket 54 is held in engagement with the lingual surface of the tooth 44 by gripping between the jaws 46 and the plate 78, light of wavelength appropriate to the adhesive used may be emitted from the source, through the plate 78 and through the tooth 44 to cure the adhesive.

A tooth engaging arm 84 extends through the open end 82 of the handle member 14 and comprises bifurcated arms 86 which terminate in a V-shaped notch 88. A similar V-shaped notch 90 is provided in the upper surface 66 of the handle member 14 at the opening 82 to permit visual alignment of the device 10 relative to the tooth 44. The bifurcated nature of the arms 88 enables brackets or other attachments to be placed over sharply pointed cusps with ease.

The tooth engaging arm 84 extends from an elongate arm member 92 which extends within the handle member 14 and is anchored adjacent the spring 74. A rotatable knob 94 is screw-threaded via a spindle into the top surface 66 of the body member 14 for engagement by an operator of the device and engages at its lower end to the elongate arm member 92.

Rotation of the knob 94 causes the arm 92 and hence the bifurcations 86 to move up or down, depending on the direction of rotation. The bifurcations 86 are intended to engage the crown surface of the tooth 44. When the plate 78 is in engagement with the facial side of the tooth 44, engagement of the crown of the tooth 44 determines the vertical location of the plate 78 and the jaws 46 with respect to the tooth 44. By varying the location of the bifurcations 86 with respect to the vertical height of the opening 82 and hence with respect to the plate 78, the orthodontic bracket 54 or other orthodontic attachment, may be positioned in any desired vertical location on the lingual side of the tooth 44.

Turning now to consideration of FIG. 4, there is illustrated therein a modification of the placement device 10 which permits the placement of orthodontic brackets or other orthodontic attachments on the facial side of teeth.

A facial placement device 110 comprises two handle members 112 and 114. The handle members 112 and 114 are constructed and mounted relative to one another substantially similarly to handle members 14 and 16 in FIGS. 1 to 3, except that the spring action of spring 56 is reversed.

In the embodiment of FIG. 4, a lever 116 is provided at the rearward end of an elongate portion 118 of the handle member 114, which a spring engaging tab 120 depends from the forward end of portion 118. The compression spring (not shown in FIG. 4 but analogous to spring 56) is mounted between the tab 120 and an abutment equivalent to abutment 60 but at the opposite end of the recess in the handle portion 112 equivalent to recess 58.

A tooth engaging plate 122 is pivotally mounted by pivot 124 to the extremity of a tooth bridging arm 126 which extends from the handle portion 112. Orthodontic attachment gripping jaws 128 are attached to the portions of the handle member 114 and located between the plate 122 and the handle portion in spaced relationship therewith.

This structure permits, upon engagement of the lingual side of the tooth by the plate 122, movement of an orthodontic attachment, such as a bracket, gripped by the jaws 128 into engagement with the facial side of a tooth, as the handle member 114 moves towards its extended location under the biasing action of the spring acting on the tab 120.

Bifurcated crown-engaging arms 130 are provided and are manipulated and function in analogous manner to bifurcations 86 described above with respect to FIGS. 1 to 3. A rotatable knob (not shown) but equivalent to knob 94 effects movement of the bifurcated arms 130 to the desired vertical position. V-shaped notches 132 and 134 equivalent to and for the same function as notches 88 and 90 in the device of FIGS. 1 to 9 also are provided.

Referring now to the embodiment of FIGS. 5 to 9, there is illustrated therein a lingual placement device 210 constructed in accordance with another preferred embodiment of the invention and is somewhat similar in appearance and structure to the embodiment of FIGS. 1 to 3.

The device 210 includes a handle 212 comprised of two handle members 214 and 216. The handle member 214 is of elongate structure of substantially inverted U-channel cross-section and may have finger notches 218 adjacent the rear end thereof to assist in gripping the handle 212.

The handle member 216 is slidably mounted to the handle member 214 by the provision of elongate slots 220 and 222 in the handle member 216 receiving pins 224 and 226 respectively mounted to one side of the handle member 214, and having heads of diameter greater than the width of the respective slot.

The handle member 216 includes a first elongate plate member 228 which is slidably mounted in face-abutting relationship with the side wall 230 of the hollow handle member 214. The handle member 216 also includes a second plate member 232 which has a portion 234 extending in fixed abutting relationship with the first plate member 228, a portion 236 diverging outwardly away from the first plate member 228, a portion 238 bridging the handle member 214 and a portion 240 extending parallel to the opposite side of the handle member 214.

Figures 5, 8, 9:
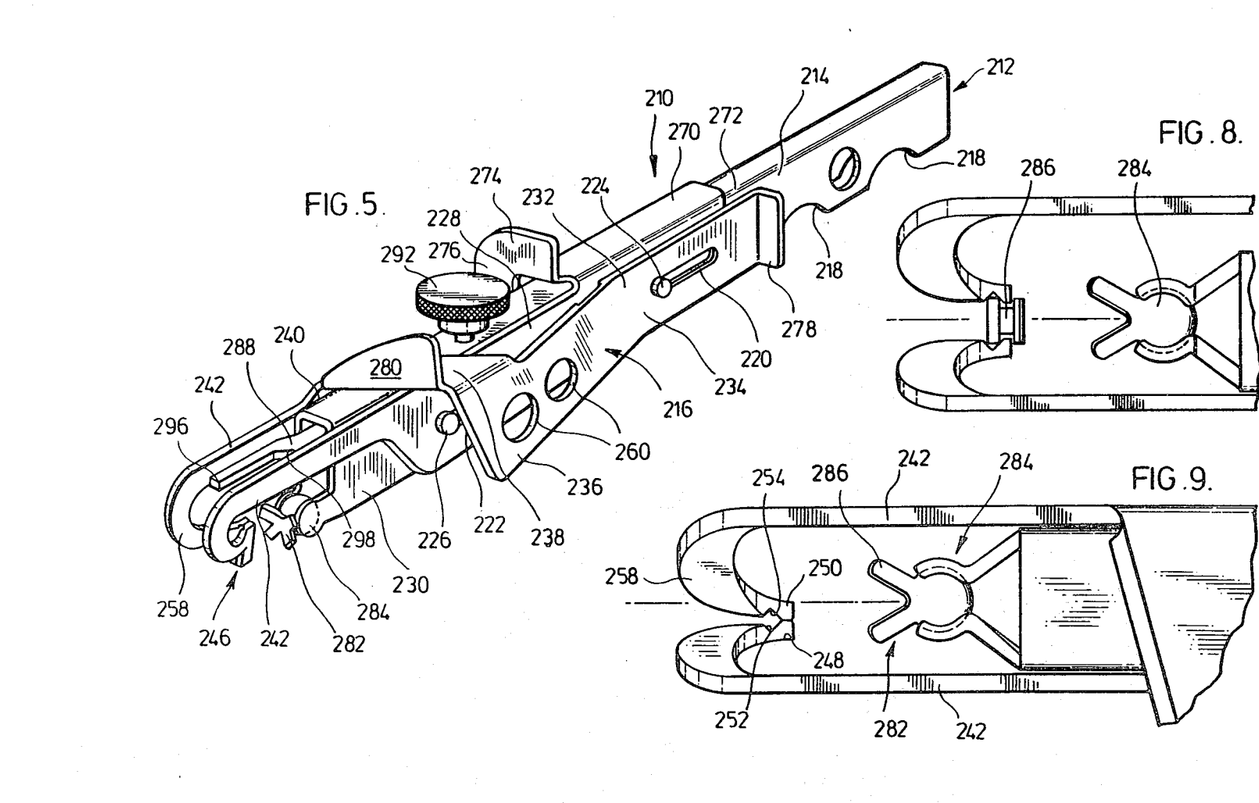
FIG. 5 is a perspective view of an orthodontic bracket placement device for the lingual placement of brackets in accordance with a further embodiment of the invention.
FIGS. 8 and 9 are elevational views of the device of FIG. 5, with the tooth rest removed for clarity, showing the device gripping (FIG. 8) an orthodontic bracket and at rest (FIG. 9).

The handle member 216 further includes a pair of parallel forwardly-directed elongate arms 242 providing a bridge over a tooth to which the orthodontic bracket is to be applied. Orthodontic attachment holding jaws 246 are provided at the extremities of the arms 242. The jaws 246 comprise a pair of vertically-depending fingers 248 and 250. The jaws 248 and 250 are provided with a pair of opposed notches 252 and 254 which assist in gripping an orthodontic bracket 256 therebetween. As may be seen in FIGS. 8 and 9, one jaw 248 is offset from the centre line of the device 210, so that, when a bracket 256 is gripped between the jaws 248 and 250, the jaws are approximately equally spaced from the centre line of the device 210, for ease of accurate location of the bracket 256 on the tooth surface. The jaws 248 and 250 are joined to the arms 242 by outwardly curved members 258.

The handle member 216 is constructed of resilient rigid material, such as spring steel, so that an orthodontic attachment, such as, bracket 256, may be gripped between the jaw fingers 248 and 250. The application of pressure, such as by a thumb, to the divergent portion 236 moves the divergent portion 236 towards the plate 28 and causes the jaw fingers 248 and 250 to open to release grip on the bracket 256. Release of pressure on the divergent portion 236 permits the divergent portion 236 to be resiliently restored to its rest position and cause the jaws 248 and 250 to close. Circular openings 260 provided in the divergent portion 236 assist in locating a pressure-applying thumb on the surface thereof.

Figure 6:
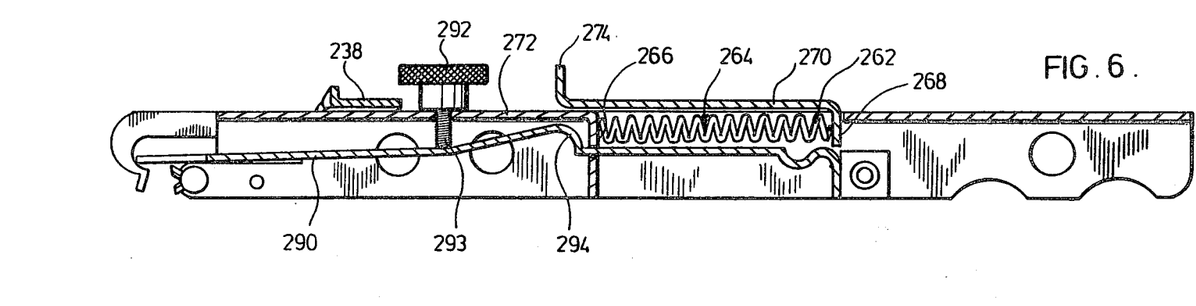
FIG. 6 is a sectional view of the bracket placement device of FIG. 5.
Figure 7:
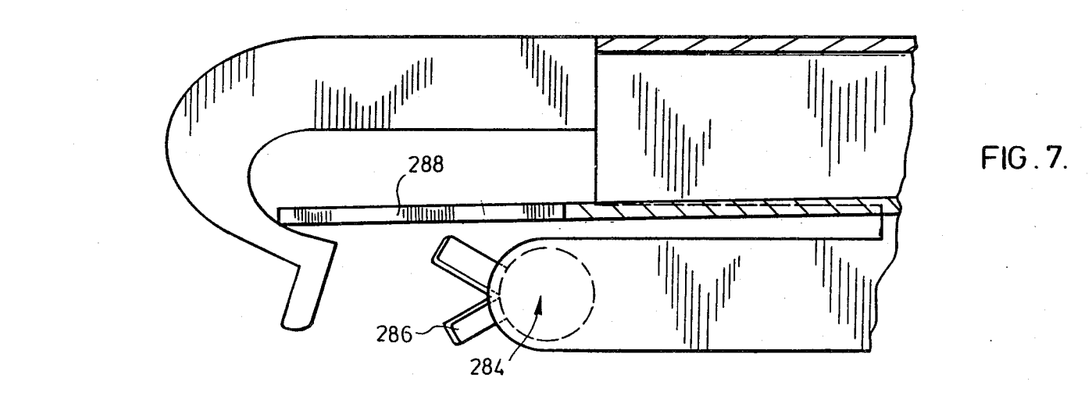
FIG. 7 is a close-up side elevational view of the bracket placement device of FIG. 5.

As in the case of the structure of the embodiment of FIGS. 1 to 3, the handle member 216 normally is biased by a compression spring 262 to a retracted position with respect to the handle member 214. The compression spring 262 is located in an elongate recess 264 in the handle member 214 and engages, at one end, an abutment 266 formed in the handle member 214. A tab 268 depending from the rearward end of an elongate portion 270 of the member 228 located adjacent the upper surface 272 of the handle member 214. An upwardly-extending lever 274 is provided at the forward end of the elongate portion 270 and has a portion 276 which extends perpendicular to the opposite side wall of the handle 214 from the side wall 230. The upstanding lever 274 permits the handle member 216 to be moved forwardly towards an extended position thereof with respect to the handle portion 214, as the spring 262 is compressed.

A stop in the form of a spring-loaded ball as described with respect to the embodiment of FIGS. 1 to 3 may be used to prevent rearward movement of the handle member 216 from its fully-extended position under the influence of the spring 262. Release of the stop may be achieved by the application of rearwardly-directed pressure on the lever 274, or lever arm 278 upstanding from the rearward end of the member 216, or on lever arm 280 upstanding from member 238.

A tooth engaging member 282 is mounted for universal movement by a ball-and-socket connection 284 to the handle member 214 spaced from the jaws 246. The tooth engaging member 282 has upper and lower pairs 286 of fingers which project towards the jaws 246, and outwardly from one another. The upper pair 286 extend for a greater distance than the lower pair 286, as may be seen in FIG. 7.

The tooth engaging member 282 is intended to engage the facial side of a tooth while an orthodontic bracket 256 is drawn into engagement with the lingual side of the tooth under the influence of the compression spring 262. The bracket 256 then is gripped in engagement with the tooth between the jaws 246 and the pairs of fingers 286.

The universal-movement mounting of the tooth-engaging member 282 and the different extent of projection of the pairs of fingers enables the device to be used effectively while accommodating different contours of tooth surface.

A tooth engaging arm 288 extends from an elongate arm member 290 which extends within the handle member 214 and is anchored within the handle, as seen in FIG. 6. A rotatable knob 292 is screw-threaded by a spindle 293 into the top surface 272 of the body member 211 and projects into engagement with the upper surface of the arm 290, which is resiliently upwardly sprung by radius 294. Rotation of the knob 292 to cause the spindle 293 to move downwardly moves the arm 290 and hence the tooth engaging arm 292 to move towards the tooth engaging member 282 (as illustrated in FIGS. 6 and 7), while rotation of the knob in the opposite direction permits the arm 290 to move away from the tooth engaging member 282 as resilient tension is released (as illustrated in FIG. 5).

The tooth engaging arm 288 is intended to engage the crown surface of the tooth when the fingers 286 are in engagement with the facial side of the tooth, engagement of the crown of the tooth determines the vertical position of the fingers 286 and the jaws 246 with respect to the tooth, so that the bracket 256 may be positioned in any desired vertical location on the lingual side of the tooth.

The tooth engaging arm 288 comprises bifurcated arms 296 which terminate in a V-shaped notch 298. The bifurcated nature of the arms 296 enables brackets or other attachments to be placed over sharply pointed cusps with ease. The V-shaped notch 298 assists in providing a sightline for accurate positioning of the bracket.

OPERATION

In operation of the device 10, the handle is gripped by the physician at the rearward end, with, if desired, one finger resting in the depression 15 to improve the grip on the handle. The thumb of the hand gripping the handle then can be used to achieve the various manipulative functions of the device 10.

An orthodontic bracket 54 is mounted between the jaw fingers 48 and 50 by forcing the jaw fingers apart and gripping the bracket 54 therebetween. After a dental cement is applied to the tooth-engaging surface of the bracket 54, the lever 68 is pushed forward against the biasing of spring 56 to move the jaws 48 and 50 away from the plate 78 until the stop ball 70 is activated to prevent rearward movement. The bridging arms 42 are positioned over the tooth 44 to which it is desired to affix the bracket 54. The plate 78 is positioned in engagement with the facial surface of the tooth while the bifurcated arms 84 rest on the crown of the tooth 44. The pivot action of the plate 78 about pivot 80 enables the device 10 to be properly angled in any particular area of the mouth so that the bracket 54 can be properly positioned with respect to the tooth 44.

Once the plate 78 has been positioned in engagement with the facial surface of the desired tooth 44 and the bifurcated arms 84 rest on the crown of the tooth 44, the knob 94 may be rotated to establish the relative vertical position of the bracket 54 and the lingual tooth surface. If desired, the vertical position of the bifurcated arms 84 may be preset by appropriate manipulation of the knob 94, as described further below. The member 16 is then released from the ball 70 by drawing on the lever 68 and the lever 68 then is allowed to retract under the influence of spring 56 to draw the bracket 54 into engagement with the lingual tooth surface, thereby gripping the tooth 44 between the plate 78 and the bracket 54. Once the cement has cured sufficiently for the bracket 54 to adhere to the lingual tooth surface, the bracket 54 is released from the jaw fingers 48 and 50 by depression of the divergent portion 34 towards the handle member 14. The device 10 then is withdrawn from the mouth and the jaws 48 and 50 permitted to close by release of pressure on the divergent portion 34.

As noted previously, the vertical position of the device 10 and hence the jaws 48 and 50 with respect to a tooth 44 may be preset and predetermined by appropriate manipulation of the knob 94. The ability to perform in this manner leads to a novel orthodontic technique, wherein a model of the teeth of the patient's mouth first is prepared and the exact location of each bracket required with respect to each tooth is determined on the model. The position of the bifurcated arms 86 is set for each tooth in accordance with the predeterminations and the bracket then is applied to the tooth accordingly.

The operation of the device 110 of FIG. 4 is analogous to that of device 10 of FIGS. 1 to 3. The only significant difference is that the lever 116 is drawn along the handle member 112 away from the tooth, rather than the lever 68 being pushed towards the tooth in the case of device 10, prior to positioning of the device 110 with respect to the tooth and is subsequently permitted to move towards the tooth to bring the bracket into engagement with the facial side of the tooth and to establish the gripping relationship between the plate 122 and the bracket.

The device 210 functions in analogous manner to device 10 as will be apparent from the detailed description of that device and the manner of operation of device 10, so that additional description with respect thereto is not required.

The orthodontic attachment placement devices 10, 110 and 210, therefore, are able to effectively and accurately position an orthodontic bracket or other orthodontic attachment at any desired location in a patient's mouth by simple and easy adjustments. The complete accuracy of positioning of attachments, absent from prior art devices, is attained in this invention. The lingual placement devices 10, 110 and 210 enable the expense of prior art transfer trays and the time consuming nature of the operations resulting from the use thereof to be overcome.

The handle members 14 and 16, 112 and 114, and 212 and 214 may be stamped from any convenient construction material, typically stainless steel and roll-formed to the desired shape. The device of the invention, therefore, is readily and easily fabricated.

SUMMARY OF DISCLOSURE

In summary of this disclosure, the present invention provides an orthodontic placement device which is versatile in positioning orthodontic attachments in any desired location in the mouth of a patient. Modifications are possible within the scope of the invention.

What we claim is:

1. A placement device for orthodontic attachments, comprising:
    tooth engaging means for engaging one side of a tooth,
    orthodontic attachment holding means for holding an orthodontic attachment in engagement with the opposite side of a tooth,
    means for moving said attachment holding means in a horizontal direction towards and away from said tooth engaging means for bringing an orthodontic attachment into engagement with the opposite side of a tooth when said tooth engaging means is in engagement with the one side of the tooth,
    means for moving said attachment holding means in a vertical direction for positioning an orthodontic attachment in a desired vertical location with respect to the opposite side of a tooth when the tooth engaging means is in engagement with the one side of the tooth, and
    handle means operatively connected to said tooth engaging means and to said attachment holding means.

2. The device of claim 1 wherein said tooth engaging means comprises a plate which is pivotally mounted to said handle for movement about a generally horizontal axis extending transverse to the axis of the handle, whereby the handle may be moved upwardly or downwardly about said generally horizontal axis when the plate is in engagement with the one side of the tooth.

3. The device of claim 2 wherein said tooth engaging plate is formed of a light-permeable material and said plate has a light emitting source operably connected thereto, whereby, upon engagement of said plate with the one side of the tooth and engagement of the orthodontic attachment to the other side of the tooth, light-curable adhesive used to attach the orthodontic attachment to the other side of the tooth may be cured by emission of light from the source through the plate and the tooth.

4. The device of claim 3 wherein the light is visible light.

5. The device of claim 1 wherein said tooth engaging means is mounted to said handle by a ball-and-socket joint to permit universal movement of said handle means when said tooth engaging means is in engagement with the one side of the tooth.

6. The device of claim 1 wherein said orthodontic attachment holding means comprises a pair of jaw members adapted to grip an orthodontic attachment therebetween.

7. The device of claim 1 wherein said handle comprises a pair of elongate relatively longitudinally movable members, said tooth engaging means is attached to one of said handle members and said holding means is attached to the other of said handle members whereby relative longitudinal movement of said handle members effects said movement of said holding means in a horizontal direction towards and away from said tooth engaging means.

8. The device of claim 7 wherein said means for moving said attachment holding means in a vertical direction comprises second tooth engaging means for engaging a crown surface of said tooth when said first mentioned tooth engaging means is in engagement with the one surface of the tooth, and means for moving said second tooth engaging means vertically relative to said handle.

9. A lingual placement device for orthodontic attachments, comprising:
   elongate handle means comprising a first handle member and a second handle member mounted to said first handle member for sliding longitudinal movement relative thereto between a first retracted position and a second extended position;
   spring means normally biasing said second handle member towards said retracted position and actuating means for moving said second handle member towards said extended position;
   tooth engaging means mounted to said first handle member for movement at least about a generally horizontal axis extending transverse to the axis of the handle;
   orthodontic attachment holding means attached to said second handle member and being horizontally spaced from said tooth engaging means, whereby, upon engagement of the facial side of a tooth by said tooth engaging means, movement of said second handle member from said extended position towards said retracted position under the biasing influence of said spring means moves said attachment holding means in a horizontal direction and brings an orthodontic attachment held thereby into engagement with the lingual side of a tooth; and
   tooth engaging arm means extending generally axially from said handle means for engagement with the crown surface of a tooth and means for moving said arm means vertically towards and away from said tooth engaging means, whereby, movement of said arm means to a specific location relative to said tooth engaging means permits, upon engagement of the facial side of a tooth by the tooth engaging means and the crown surface by the arm, positioning of an orthodontic attachment in a desired vertical location with respect to the lingual side of the tooth.

10. The device of claim 9 wherein said tooth engaging means comprises a plate which is pivotally mounted to said first handle member for pivotal movement only about said generally horizontal axis.

11. The device of claim 9 wherein said tooth engaging means is mounted to said first handle means by a ball-and-socket connection to permit universal movement relative to said handle including about said generally horizontal axis.

12. The device of claim 11 wherein said tooth engaging means comprises finger means extending divergently from said ball-and-socket connection to engage said facial tooth surface.

13. The device of claim 9 wherein said second handle member is constructed of resilient rigid material and comprises a first elongate plate member slidably mounted in face-abutting relationship with one side of the first handle member, and a second elongate plate member mounted in face-abutting relationship with said first plate member for a portion of the length thereof and having a portion diverging outwardly away from said first plate member, a portion bridging said first handle member and a portion slidably engaging the opposite side of said first handle member, said first and second members terminating in jaw members which cooperate to grip an orthodontic attachment therebetween, whereby movement of said divergent portion of said second plate member towards said first plate member causes said jaws to open and resilient restoration of said divergent portion causes said jaws to close.

14. The device of claim 13 wherein said jaw members comprises a pair of vertically-extending fingers attached to the respective plate members of said second handle member by a first curved portion which curves outwardly from the jaw member to form a generally U-shape with each other and a second elongate portion which bridges over a tooth when the plate means is in engagement with the facial side of the tooth.

15. The device of claim 14 wherein said jaw members have opposed notches in the surface thereof to assist in gripping an orthodontic attachment therebetween.

16. The device of claim 14 wherein said jaw members are arranged with a first jaw member offset from the vertical centre line of the first handle member, so that upon opening of the jaw members to grip an orthodontic attachment therebetween, the jaw members are approximately equally spaced from said vertical centre line.

17. The device of claim 14 wherein said actuating means for said second handle member comprises a member upstanding from a forward end of a portion of said first plate member of the second handle member slidably engaging the upper surface of the first handle member, said spring means is a compression spring recessed in first handle member in engagement at one end with an abutment formed in said first handle member and at the other end with a tab depending from the rearward end of said last-mentioned first plate member portion, whereby, upon movement of said lever forwardly of the device, said spring is compressed as said jaw members move away from said tooth engaging means and, upon release of the compressive force, the spring relaxes and the jaw members move towards said tooth engaging means.

18. The device of claim 9 wherein said first handle member has a generally inverted U-shape in cross section.

19. The device of claim 9, wherein said tooth engaging arm means comprises bifurcated arms extending forwardly through an open end of said first handle member and an elongate arm extending within said first handle member to an anchor at an end thereof remote from said bifurcated arm, and said arm moving means comprises a rotatable knob fixedly mounted on an axle extending in threaded engagement with said disk handle member and operably connected to the elongate arm, whereby, upon rotation of said wheel, said elongate arm, and hence said bifurcated arms, is moved up or down.

20. The device of claim 19, wherein said bifurcated arms terminate in a V-notch and a similar V-notch is provided in the upper side of said first handle member to permit visual alignment of the device relative to a tooth.

21. The device of claim 9 including releasable stop means for holding said second handle member in said extended position.

22. The device of claim 21 wherein said releasable stop means comprises ball means spring biased to protrude through an opening in one side of said first handle member and engage a rearward end of said second handle member when the latter is in said extended position.

23. A facial placement device for orthodontic attachments, comprising:
   elongate handle means comprising a first handle member and a second handle member mounted to the first handle member for sliding longitudinal member relative thereto between a first retracted position and a second extended position;
   spring means normally biasing said second handle member towards said extended position and actuating means for moving said second handle member towards said retracted position;
   tooth engaging means mounted to said arm means extending from first handle member for movement at least about a generally horizontal axis extending transverse to the axis of the handle;
   orthodontic attachment holding means attached to said second handle members and being located between said tooth engaging means and said first handle member in horizontally-spaced relationship with respect to said tooth engaging means, whereby, upon engagement of the lingual side of a tooth by said tooth engaging means, movement of said second handle member from said retracted position towards said extended position under the biasing influence of said spring means moves said attachment holding means in a horizontal direction and brings an orthodontic attachment held thereby into engagement with the facial side of a tooth; and
   tooth engaging arm means extending generally axially from said handle means for engagement with the crown surface of a tooth and means for moving said tooth engaging arm means vertically towards and away from said tooth engaging means, whereby, movement of said arm means to a specific location relative to said tooth engaging means permits, upon engagement of the lingual side of a tooth by the tooth engaging means and the crown surface by the arm, positioning of an orthodontic attachment in a desired vertical location with respect to the facial side of the tooth.

24. The device of claim 23 wherein said tooth engaging means comprises a plate which is pivotally mounted to said arm means for pivotal movement only about said generally horizontal axis.

25. The device of claim 24 wherein said arm means to which said tooth engaging plate is attached bridges over a tooth when the plate means is in engagement with the lingual side of the tooth.

26. The device of claim 23 wherein said second handle member is constructed of resilient rigid material and comprises a first elongate plate member slidably mounted in face-abutting relationship with one side of the first handle member, and a second elongate plate member mounted in face-abutting relationship with said first plate member for a portion of the length thereof and having a portion diverging outwardly away from said first plate member, a portion bridging said first handle member and a portion slidably engaging the opposite side of said first handle member, said first and second members terminating in jaw members which cooperate to grip an orthodontic attachment therebetween, whereby movement of said divergent portion of said second plate member towards said first plate member causes said jaws to open and resilient restoration of said divergent portion causes said jaws to close.

27. The device of claim 26 wherein said jaw members comprise a pair of vertically-extending fingers attached to the respective plate members of said second handle member by curved portions which curve outwardly and upwardly to form a generally U-shape.

28. The device of claim 27 wherein said actuating means for said second handle member comprises a lever member upstanding from a rearward end of a portion of said first plate member of said second handle member slidably engaging the upper surface of the first handle member, said spring means is a compression spring recessed in said first handle member in engagement at one end with an abutment formed in said first handle member and at the other end with a tab depending from the forward end of the last-mentioned first plate member portion, whereby, upon movement of said lever rearwardly of the device, said spring is compressed as said jaw members move away from said tooth engaging means and, upon release of the compressive force, the spring relaxes and the jaw members move towards said tooth engaging means.

29. The device of claim 28, wherein said tooth engaging arm means comprises bifurcated arms extending forwardly through an open end of said first handle member and an elongate arm extending within said first handle member to an anchor at an end thereof remote from said bifurcated arm.

30. The device of claim 29, wherein said bifurcated arms terminate in a V-notch and a similar V-notch is provided in the upper side of said first handle member to permit visual alignment of the device relative to a tooth.

* * * * *